(12) United States Patent
Hopewell

(10) Patent No.: US 6,308,532 B1
(45) Date of Patent: Oct. 30, 2001

(54) SYSTEM AND PROCESS FOR THE RECOVERY OF PROPYLENE AND ETHYLENE FROM REFINERY OFFGASES

(75) Inventor: Richard B. Hopewell, Medfield, MA (US)

(73) Assignee: Chart Industries, Inc., Mayfield Hts, OH (US)

( * ) Notice: Subject to any disclaimer, the term of this patent is extended or adjusted under 35 U.S.C. 154(b) by 0 days.

(21) Appl. No.: 09/463,466
(22) PCT Filed: Nov. 19, 1999
(86) PCT No.: PCT/US99/27622
  § 371 Date: Jan. 20, 2000
  § 102(e) Date: Jan. 20, 2000
(87) PCT Pub. No.: WO00/31214
  PCT Pub. Date: Jun. 2, 2000

Related U.S. Application Data
(60) Provisional application No. 60/109,360, filed on Nov. 20, 1998.

(51) Int. Cl.⁷ .................................................... F25J 1/00
(52) U.S. Cl. ............................................ 62/620; 62/935
(58) Field of Search ..................................... 62/620, 935

(56) References Cited

U.S. PATENT DOCUMENTS

| | | | |
|---|---|---|---|
| 4,430,102 | * 2/1984 | Tedder | 62/935 |
| 4,753,667 | * 6/1988 | O'Connell | 62/935 |
| 5,345,772 | 9/1994 | Hopewell . | |
| 5,546,764 | 8/1996 | Mehra . | |
| 5,680,775 | * 10/1997 | Manley | 62/935 |

OTHER PUBLICATIONS

"Refiners Get Cracking on Petrochemicals"; *Chemical Engineering*; May 1999, pp. 30–33, (except p. 32, which contains advertising only).

* cited by examiner

*Primary Examiner*—Ronald Capossela
(74) *Attorney, Agent, or Firm*—Calfee, Halter & Griswold LLP

(57) ABSTRACT

A system and process for the recovery of ethylene and propylene from a gas stream, such as a refinery offgas stream. The process comprises withdrawing, cooling, and recovering an overhead vapor stream from a single distillation column. The process includes withdrawing a liquid $C_3+$, $C_4+$, $C_5+$ or $C_6+$ bottoms product stream and recycling a portion of the bottoms steam to maintain an overhead column condenser at temperature refrigeration levels of above −140° F. and withdrawing a vapor side stream rich in propylene or ethylene-propylene.

24 Claims, 1 Drawing Sheet

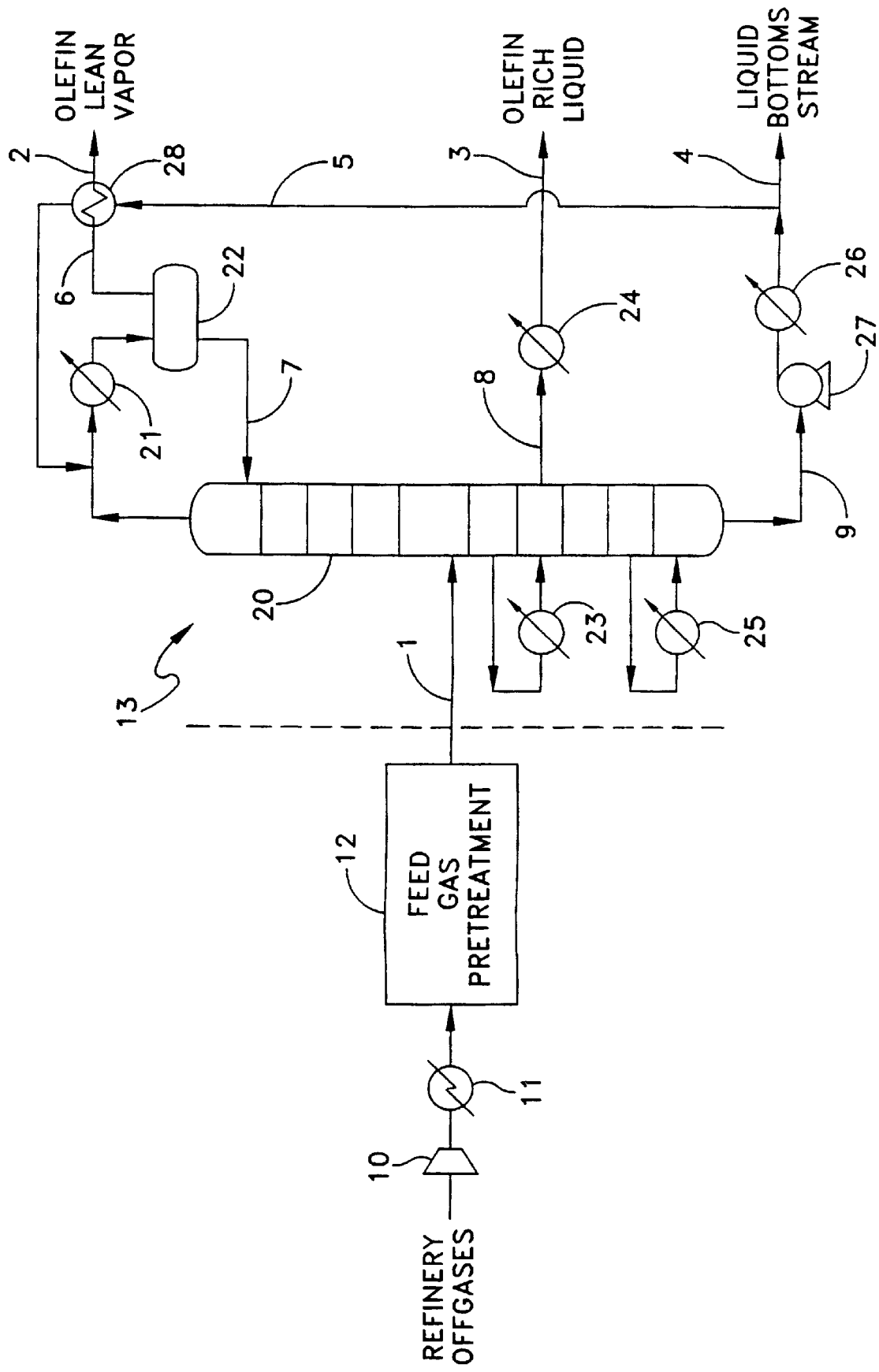

SYSTEM AND PROCESS FOR THE RECOVERY OF PROPYLENE AND ETHYLENE FROM REFINERY OFFGASES

REFERENCE TO PRIOR APPLICATION

This application incorporates by reference and claims the benefit of the priority date of U.S. Provisional Patent Application Ser. No. 60/109,360, filed Nov. 20, 1998.

BACKGROUND OF THE INVENTION

Petrochemical offgases, such as refinery offgases from Fluid Catalytic Cracker Units (FCCU) or Coker units, generally comprise an offgas mixture which comprises: hydrogen; nitrogen; carbon monoxide; ethane; ethylene; argon; propylene; as well as, butane and pentanes. In particular, the refinery offgasses from a FCCU contain olefin components, up to about 20 percent by volume ethylene and up to about 11 percent by volume propylene, which components normally are not recovered from the offgases, but which components may have value to warrant recovery and use in other petrochemical processes or uses in downstream processing. The typical range of components is listed in Table 1.

Normally, such refinery offgases are burnt and used as fuel. When the refinery FCCU is located near an ethylene or propylene plant, then recovery and downstream use of the recovered ethylene and propylene or propylene is economical. In such recovery processes, ethylene and propylene are recovered together and then directly or separately recovered from the mixture.

In the publication, Chemical Engineering, May 1999, pages 30–33, "Refiners Get Cracking on Petrochemicals" hereby incorporated by reference, the attributes of Fluid Catalytic Cracker (FCC) technology are explained. Propylene is increasing in demand, since it is a feedstock for polypropylene. About 30 percent (30%) of the global demand is a byproduct of FCC operations for producing gasoline. Over the next five years, the growth in demand is anticipated at over 5 percent (5%) per year. In response to this demand, FCC process technology is being modified to enhance olefin's production. Thus, the current yield of 5 percent (5%) of the feedstock converted to propylene is being increased to about 35 percent (35%), while the ethylene yield is increased from about 1 to 4 percent (1–4%).

Another option is the reaction of ethylene with 2-butene to produce propylene, termed metathesis. Thus, the recovery of these components from a FCC provides the opportunity for further propylene yields.

U.S. Pat. No. 5,546,764, issued Aug. 20, 1996, and incorporated herein by reference, discloses an absorption process for recovering ethylene from a feed gas stream in an absorber stripper employing a heavy hydrocarbon absorption solvent, the absorber stripper bottoms stream is then fractionated to produce an overhead, ethylene product stream.

The recovery of valued olefin components from offgasses may be accomplished by partial condensation from the offgas feed stream; however, such recovery requires low temperatures, e.g., about —150° F. or lower. These low temperatures require refrigeration supplied by turboexpander processes and heat exchangers with multi-pass plate fin heat exchangers. This type of equipment is not used extensively in oil refineries. Furthermore, the use of such low temperatures increases the possibility of gum formation by the reaction of NOX compounds with butadiene, which gums may be explosive when the plant is shut down and warmed up for restart.

U.S. Pat. No. 5,345,772, issued Sept. 13, 1994, shows a single column process with Natural Gas Liquid (NGL) recycled to the upper zone of the column. This process is applied to the recovery of the paraffinic components of propane or ethane from gas streams with a high $CO_2$ content. These gases are encountered in enhanced oil recovery projects where the $CO_2$ content of the gas stream may be 83 percent (83%), as shown in the patent example.

It is desirable to provide a system and process for the recovery of olefins from offgases at warmer temperatures, such as propane refrigeration levels, to avoid the disadvantages of prior art recovery processes and systems and to provide other economic and process efficiency advantages.

SUMMARY OF THE INVENTION

The invention relates to a system and process for the recovery of olefins from petrochemical offgases. In particular, the invention concerns the recovery of ethylene and propylene or propylene from refinery offgases from a Fluid Catalytic Cracker Unit (FCCU) of a refinery at propane refrigeration temperatures.

The process provides for maintaining the overhead condenser temperature by the use of the liquid bottoms recycle stream from the single column. Generally, the overhead condenser is maintained at above –140° F., but depending on the olefin component to be recovered, the overhead condenser temperature may range, for example, from above about –114° F. for ethylene recovery or above about –35 to –40° F. for propylene recovery, or within a range of about –20° F. to –114° F. for a mixture of ethylene and propylene.

The system and process generally comprises a single distillation column to receive an olefin-containing, hydrocarbon gas stream and maintaining the overhead condensation temperature at a warmer temperature than –150° F., such as, at a refrigeration temperature level of above –140° F., by recycling a heavy $C_3$+ bottoms stream from the single column, to the overhead condenser or upper section of the distillation column, and withdrawing a liquid bottoms stream; a vapor side stream rich in the selected olefin; and an overhead vapor stream lean in the olefin components.

The system and process of the invention comprises a system and process for the recovery of olefin components, such as: ethylene; propylene; or combinations thereof from a refinery offgas, such as: a FCCU; a reformer; a Coker offgas; or other olefin gas source, which process comprises: introducing the gas feed stream into a recovery distillation column with an overhead condenser; withdrawing a liquid bottoms product stream from the recovery column; recycling at least a portion of the liquid or lower section bottoms product stream into the overhead condenser or into an upper tray section, e.g., top 5 to 10 trays of the recovery column, to warm the overhead condenser; maintaining with the recycled product stream, the overhead condenser at selected propane, propylene, or ethylene refrigeration levels of above –140° F. and generally above –114° F.; withdrawing a heavy liquid product stream from the recovery column; withdrawing a vapor phase side downstream from the column, which side downstream is rich in the olefin components to be recovered; and condensing and recovering the selected olefin components from the vapor phase side downstream, for downstream processing use; and withdrawing an olefin lean, overhead vapor stream from the overhead condenser or an upper section of the recovery column; and optionally, employing the lean overhead vapor stream as regenerated gas in the dehydration of the feed gas stream, fuel use, or other use.

Typically, and optionally, the refinery offgas feed stream process includes: pretreating steps of water washing to remove impurities; removing acid gases, like carbon dioxide and hydrogen sulfide; and dehydrating the offgas feed stream. The process may be directed to the recovery of propylene or ethylene-propylene, generally, for downstream processing use, such as, where an ethylene-propylene petrochemical plant is located near the offgas source.

The system and process provide multiple economic and process advantages over prior art systems and processes to include, but not be limited to: eliminating the requirement of a separate column to produce the $C_4$+ recycle stream, while only propane level refrigeration is required in some instances for the system and process. The system and process eliminate the formation of dangerous and explosive prior art gum formation, because of the relatively warm refrigeration level temperatures employed.

When propane refrigeration alone is used, the process permits the use of a carbon steel column and carbon steel shell and tube heat exchangers, due to the propane or higher temperature refrigeration levels and no expensive turboexpanders are employed. While in one embodiment illustrated, acid gas removal occurs in the offgas feed stream, the acid gas need not be removed upstream of the recovery column, because of potential freezing in the recovery column as in prior art cryogenic systems, but may be removed downstream of the recovery column. In the system and process, less severe dehydration of the offgas feed stream is required than for a low temperature cryogenic system, so that glycol-based dehydration may be used, e.g., the DRIZO® process (DRIZO is a registered trademark of OPC Design, Inc. for a gas dehydration system). The system and process provide for high olefin recovery, for example, from a FCCU offgas, about 98%+ for propylene, with low $C_2/C_3$ ratios of less than about 0.01, and about 90%+ for ethylene.

The process and system can be used for the recovery of ethylene and ethane for the offgases; however, the utility consumption will be higher, and the $C_2$ components of the offgas now become the side downstream along with the $C_3$ components.

The system and process shall be described for the purposes of illustration only in connection with certain embodiments; however, it is recognized that various changes, additions, improvements and modifications to the illustrated embodiments may be made by those persons skilled in the art, all falling within the spirit and scope of the invention.

BRIEF DESCRIPTION OF THE DRAWING

The drawing is a schematic illustration of the process and system for the recovery of propylene from a Coke or FCCU offgas source.

DESCRIPTION OF THE EMBODIMENTS

The same general system and process configuration in the drawing can be employed for either propylene (and heavier components) recovery or ethylene (and heavier components), including propylene recovery.

In the drawing, process steps are designated by the 10, 11, 12, 13 series. Process equipment within step 13 is designated by the 20, 21 . . . series. Process streams within step 13, designated by the 1, 2 . . . series.

The refinery offgases considered in this described embodiment are the combined FCCU and Coker gases. The gases are at low pressure, near atmospheric pressure, they are compressed to about 270 psig in compressor 10, cooled in exchanger 11 to 100° F., and then processed in stages in a pretreatment step 12. These stages may be comprised of a waterwash; an amine contactor column for $H_2S$ removal or other acid gas removal; and a dehydration stage for water vapor removal. The treated gas stream now enters the single column process 13.

The following is a description of the single column process for propylene recovery. The feed vapor 1 enters column 20 at tray 16. Tray designations are theoretical as encountered in the computer simulations. Tray 1 is the top tray, in this case, the reflux condenser 21. The two phase liquid-vapor stream from the overhead reflux condenser 21 is directed to a reflux drum 22 for reflux and separation. The separated, reflux liquid stream from reflux drum 22 is returned to the upper tray section of the column 20. The separated, overhead vapor stream 6 is withdrawn as an olefin-lean product stream.

The column has a side reboiler 23, for heat conservation purposes, at tray 33. A side vapor draw, stream 8, is extracted from the column 20 at this stage. The use and positioning of this side reboiler is important in concentrating the side draw in the desired propylene to be recovered and minimizing the ethylene component. The side reboiler 23 employs liquid from an intermediate tray of the column, below the point of introduction of the feed stream, and then after reboiling, returning the reboiled liquid to the tray below the tray from which the liquid is withdrawn. The use of a column intermediate side reboiler 23 enhances the concentration of the olefin component in the vapor side draw stream 8. The vapor side draw stream 8 is withdrawn from between the two intermediate trays used for the side reboiler 23.

The bottom reboiler 25 is tray 43. The bottoms liquid, stream 9, is pumped by 27, then cooled in 26 and split into two streams 4 and 5. Stream 5 is cooled and recycled to the condenser 21, joining the column overhead vapor stream at the condenser inlet. This stream is partially condensed by refrigerant in the reflux condenser 21. The vapor stream 6, and liquid stream 7, are separated in the reflux drum 22. The reflux is returned to the column 20. The vapor is reheated against the recycled stream 5 in the exchanger 27, simultaneously chilling this stream to –20° F.

The vapor phase side draw, stream 8, is cooled and condensed in exchanger 24; stream 3 is then the light hydrocarbon product. The split off stream 4 is exported as the heavy liquid hydrocarbon product. The reheated stream 2 goes to the refinery fuel gas stream.

The operating conditions for the column are listed in Table 2, and the overall material balance and the recycle stream flow and composition is given in Table 3.

The following features of this column simulation are important for the following reasons:

1) The column is operated at relatively low pressure, 250 psig.
2) The column's reflux condenser operates at –35° F. This level of refrigeration can be supplied by propane or propylene. The materials of construction can be carbon steel for the entire system.
3) All the propylene recovered is in the light liquid hydrocarbon stream, and 98 percent (98%) of the propylene in the feedstock is recovered in this stream. The $C_2$ and lighter components are rejected to the fuel gas. The $C_2$ specification for stream 8 is:

$$\frac{C_2H_6 + C_2H_4}{C_3H_8 + C_3H_6} = 0.005$$

4) The heavy liquid stream contains $C_4+$ components, and it is predominately $C_6+$ and has a molecular weight of 79.4. These components are available in the feed gas. The composition of this recycled stream and net heavy liquid product is dependent on their relative quantities in the feed. The recycle to feed ratio is 0.18 moles/mole.

5) The coldest temperature in the tower, i.e., $-35°$ F., is well above any potential gum deposition temperature, i.e., $-150°0$ F.

The single column, ethylene recovery process flow scheme is the same as shown in the drawing. The column operating conditions are altered to achieve the high ethylene recovery. The column conditions are listed in Table 4. The overall material balance and recycle stream flow and composition are listed in Table 5.

The features of this operation are:
1) The column operates at 250 psig, which is a considerably lower pressure than that disclosed in U.S. Pat. No. 5,546,764, issued Aug. 20, 1996, in which the absorber is operated at 550 psig, which requires higher power consumption for the feed gas compressors.
2) The overhead temperature is $-114°$ F. A cascade refrigeration system is required for this system, and stainless steel materials are required where the lower temperatures are encountered.
3) The ethylene recovery is about 90 percent (90%).

$$\text{The } \frac{CH_4}{C_2H_6 + C_2H_4} \text{ ratio} = 0.0025$$

in the recovered light liquid stream. This temperature can be set to eliminate the need for downstream demethanization of the purified ethylene.

4) The recycle stream is comprised of $C_3+$ components, which are available in the feed. A net purge, stream 4, maintains the material balance for these components. The recycle to feed ratio is 0.47 moles/mole.
5) The lowest temperature in the system is above the gum formation and deposit temperature.

The cited specific examples (supra) for propylene and ethylene recovery supply the details of stream compositions and flows and the column conditions. It is recognized that the system and process may be employed to any olefin recovery design process requirement, as appropriate.

The range of conditions for which the column may be designed is as follows:

| | |
|---|---|
| Pressure, psig | 150 to 550 |
| Condenser temperature, ° F. | −140 to 0 |
| Recycle stream composition | $C_3+$, $C_4+$, $C_5+$ or $C_6+$ |
| Recycle/feed ratio, mole/mole | 0.03 to 1.0 |
| Olefin components recovered | $C_3H_6+$ or $C_2H_4+$ |

Another embodiment of the process and system of the invention is the recovery of ethylene from synthesis gas produced by the steam cracking of hydrocarbons in an ethylene production facility. A typical gas composition contains:

| Typical Ethylene Plant Syngas | |
|---|---|
| Gas | Percentage/volume |
| $H_2$ | 23 |
| $C_1$ | 19 |
| $C_2H_4$ | 32 |
| $C_2H_6$ | 13 |
| $C_3H_6$ | 7 |
| $C_3H_8$ | 1 |
| $C_4+$ | 3 |

The ethylene plant syngas is similar to the component range shown for refinery offgases and is within the capability of the process and system of the invention.

TABLE 1

| FCC and Coker Offgas Component Concentration Ranges: | |
|---|---|
| Component | Percentage Volume |
| $H_2$ | 7 to 22 |
| $CO_2$ | 0 to 2 |
| $H_2S$ | 2 to 11 |
| $N_2$ | 1 to 17 |
| $CH_4$ | 25 to 45 |
| $C_2H_6$ | 12 to 16 |
| $C_2H_4$ | 2 to 20 |
| $C_3H_8$ | 0.5 to 8 |
| $C_3H_6$ | 2 to 11 |
| i, $nC_4H_{10}$ | 1 to 2 |
| Butenes | 0.4 to 4 |
| $C_5$ | 1 to 3 |
| $CH_4$ | |

TABLE 2

| | | Single Column Operation Propylene Recovery | | |
|---|---|---|---|---|
| TRAY | HEATER/ COOLER | PRESSURE PSIG | TEMPERATURE ° F. | DUTY MMBTU/HR |
| 1 | CONDENSER | 250 | −35 | 5.1 |
| 16 | FEED | 257 | 50 | |
| 33 | SIDE REBOIL VAPOR DRAW | 258 | 175 | 4.9 |
| 43 | REBOILER | 260 | 345 | 12.3 |

TABLE 3

Single Column Material Balance
Propylene Recovery

| Stream ID | 1 | 2 | 3 | 4 | 5 |
|---|---|---|---|---|---|
| Name | Feed | Fuel Gas | Light Liquid | Heavy Liquid | Recycle |
| Phase | Mixed | Dry vapor | Dry Liquid | Dry Liquid | Dry Liquid |

Fluid Rates, lb/mol/hr

| | | | | | |
|---|---|---|---|---|---|
| 1 $H_2O$ | .0000 | .0000 | .0000 | .0000 | .0000 |
| 2 $H_2S$ | .0295 | .0288 | 6.4850E-04 | 7.6394E-1O | 1.0955E-08 |
| 3 $N_2$ | 101.0916 | 101.0917 | 4.0918E-16 | .0000 | .0000 |
| 4 CO | 15.3521 | 15.3521 | 1.7130E-16 | .0000 | .0000 |
| 5 $CO_2$ | 14.7452 | 14.7452 | 2.3822E-06 | 1.1595E-14 | 1.6628E-13 |
| 6 $H_2$ | 287.0592 | 287.0594 | .0000 | .0000 | .0000 |
| 7 $C_1$ | 1108.8446 | 1108.8454 | 8.5987E-10 | 4.6351E-20 | 6.6471E-19 |
| 8 Ethylene | 302.8797 | 302.8713 | 8.6336E-03 | 5.9396E-10 | 8.5179E-09 |
| 9 $C_2$ | 486.4302 | 484.5020 | 1.9285 | 1.1477E-06 | 1.6459E-05 |
| 10 Propylene | 254.2555 | 5.1181 | 249.1017 | .0349 | .5000 |
| 11 $C_3$ | 138.7629 | .4241 | 138.2981 | .0402 | .5769 |
| 12 Isobutene | 18.1834 | .3218 | 17.3523 | .5092 | 7.3024 |
| 13 lButene | 25.3941 | .4805 | 24.1390 | .7745 | 11.1070 |
| 14 T2Butene | 17.9134 | .4505 | 16.4713 | .9915 | 14.2194 |
| 15 C2Butene | 12.9536 | .3417 | 11.7580 | .8538 | 12.2442 |
| 16 13Butd | .3810 | 7.2268E-03 | .3614 | .0124 | .1782 |
| 17 $IC_4$ | 31.2459 | .4924 | 30.1260 | .6275 | 8.9985 |
| 18 $NC_4$ | 23.5549 | .7016 | 21.6213 | 1.2319 | 17.6671 |
| 19 3M1Butene | .3733 | .0124 | .2993 | .0616 | .8838 |
| 20 1Pentene | 6.1519 | .1679 | 4.6490 | 1.3349 | 19.1431 |
| 21 2M1Butene | 3.1259 | .0817 | 2.3595 | .6846 | 9.8181 |
| 22 2M2Butene | 5.7787 | .1175 | 4.0864 | 1.5748 | 22.5843 |
| 23 T2Pentene | 5.0993 | .1166 | 3.7056 | 1.2771 | 18.3152 |
| 24 C2Pentene | 2.9111 | .0658 | 2.1088 | .7365 | 10.5618 |
| 25 $IC_5$ | 17.3760 | .5095 | 13.2697 | 3.5967 | 51.5801 |
| 26 $NC_5$ | 8.2941 | .2025 | 6.0681 | 2.0235 | 29.0189 |
| 27 1Hexene | 22.9652 | .2497 | 13.0143 | 9.7010 | 139.1198 |
| 28 $NC_6$ | 14.8743 | .1235 | 7.9553 | 6.7954 | 97.4522 |
| 29 $NC_7$ | 5.6047 | .0152 | 2.0050 | 3.5845 | 51.4047 |
| 30 $NC_8$ | 1.1669 | 8.4490E-04 | .2554 | .9107 | 13.0599 |
| 31 $NC_9$ | .1702 | 2.30B6E-05 | .0216 | .1487 | 2.1321 |
| 32 $NC_{10}$ | .0463 | 1.4052E-06 | 3.2544E-03 | .0431 | .6178 |
| Total Rate, lb-mol/hr | 2933.0148 | 2324.4973 | 570.9684 | 37.5492 | 538.4857 |
| Temperature, °F. | 100.0 | 81.0 | 100.0 | 100.0 | 100.0 |
| Pressure, psig | 260 | 246 | 254.7 | 252 | 300 |
| Molecular weight | 26.2661 | 19.7302 | 49.3807 | 79.3944 | 79.3944 |

TABLE 4

Single Column Operation
Ethylene Recovery

| TRAY | HEATER/ COOLER | PRESSURE PSIG | TEMPERATURE °F. | DUTY MMBTU/HR |
|---|---|---|---|---|
| 1 | CONDENSER | 250 | −114 | 2.8 |
| 17 | FEED | 257 | 17 | |
| 27 | SIDE REBOIL VAPOR DRAW | 258 | 155 | 13.9 |
| 44 | REBOILER | 260 | 337 | 20.1 |

TABLE 5

Single Column Material Balance
Ethylene Recovery

| Stream ID | 1 | 2 | 3 | 4 | 5 |
|---|---|---|---|---|---|
| Name | Feed | Fuel Gas | Light Liquid | Heavy Liquid | Recycle |
| Phase | Mixed | Dry vapor | Dry Liquid | Dry Liquid | Dry Liquid |

Fluid Rates, lb/mol/hr

| | | | | | |
|---|---|---|---|---|---|
| 1 $H_2O$ | .0000 | .0000 | .0000 | .0000 | .0000 |
| 2 $H_2S$ | .0295 | 1.4165E-08 | .0295 | 6.3460E-10 | 8.7321E-08 |

TABLE 5-continued

Single Column Material Balance
Ethylene Recovery

| Stream ID<br>Name<br>Phase | 1<br>Feed<br>Mixed | 2<br>Fuel Gas<br>Dry vapor | 3<br>Light Liquid<br>Dry Liquid | 4<br>Heavy Liquid<br>Dry Liquid | 5<br>Recycle<br>Dry Liquid |
|---|---|---|---|---|---|
| 3 $N_2$ | 101.0916 | 101.0918 | 8.3535E-06 | .0000 | .0000 |
| 4 CO | 15.3521 | 15.3521 | 3.9611E-06 | .0000 | .0000 |
| 5 $CO_2$ | 14.7453 | 8.9805 | 5.7650 | 5.3078E-12 | 7.3035E-10 |
| 6 $H_2$ | 287.0592 | 287.0596 | 1.2819E-09 | .0000 | .0000 |
| 7 $C_1$ | 1108.8446 | 1106.9524 | 1.8937 | 2.6010E-16 | 3.5790E-14 |
| 8 Ethylene | 302.8797 | 31.7627 | 271.1254 | 2.8096E-08 | 3.8660E-06 |
| 9 $C_2$ | 486.4302 | .0118 | 486.4334 | 2.6369E-06 | 3.6284E-04 |
| 10 Propylene | 254.2555 | .0605 | 254.1671 | .0358 | 4.9273 |
| 11 $C_3$ | 138.7629 | .0910 | 138.6083 | .0681 | 9.3670 |
| 12 Isobutene | 18.1834 | .4567 | 17.8763 | .2600 | 35.7821 |
| 13 lButene | 25.3941 | .0635 | 24.9574 | .3725 | 51.2536 |
| 14 T2Butene | 17.9134 | .0380 | 17.5477 | .3269 | 44.9778 |
| 15 C2Butene | 12.9536 | .0238 | 12.6742 | .2549 | 35.0752 |
| 16 13Butd | .3810 | 9.1258E-04 | .3743 | 5.8301E-03 | .8023 |
| 17 $IC_4$ | 31.2459 | .1028 | 30.7498 | .3930 | 54.0781 |
| 18 $NC_4$ | 23.5549 | .0588 | 23.0823 | .4128 | 56.8034 |
| 19 3M1Butene | .3733 | 4.9747E-04 | .3606 | .0121 | 1.6673 |
| 20 1Pentene | 6.1519 | 5.3771E-03 | 5.8889 | .2567 | 35.3160 |
| 21 2M1Butene | 3.1259 | 2.5028E-03 | 2.9901 | .1328 | 18.2728 |
| 22 2M2Butene | 5.7787 | 2.9723E-03 | 5.4626 | .3120 | 42.9258 |
| 23 T2Pentene | 5.0993 | 03.2742E-03 | 4.8462 | .2489 | 34.2422 |
| 24 C2Pentene | 2.9111 | 1.7979E-03 | 2.7650 | .1438 | 19.7891 |
| 25 $IC_5$ | 17.3760 | .0169 | 16.6683 | .6883 | 94.7113 |
| 26 $NC_5$ | 8.2941 | 6.1164E-03 | 7.8942 | .3923 | 53.9813 |
| 27 1Hexene | 22.9652 | 5.2600E-03 | 20.7222 | 2.2284 | 306.6281 |
| 28 $NC_6$ | 14.8743 | 2.5264E-03 | 13.2102 | 1.6546 | 227.6777 |
| 29 $NC_7$ | 5.6047 | 1.9756E-04 | 4.3724 | 1.2264 | 168.7467 |
| 30 $NC_8$ | 1.1669 | 7.1470E-06 | .7216 | .4426 | 60.8989 |
| 31 $NC_9$ | .1702 | 1.2484E-07 | .0722 | .0972 | 13.3781 |
| 32 $NC_{10}$ | .0463 | 3.0275E-09 | .0118 | .0342 | 4.7007 |
| Total Rate,<br>lb-mol/hr | 2933.0149 | 1551.7443 | 1371.2705 | 10.0000 | 1376.0029 |
| Temperature, ° F. | 100.0 | 85.5 | 100.0 | 100.0 | 100.0 |
| Pressure, psig | 270.5 | 246.0 | 253.9 | 252 | 300 |
| Molecular weight | 26.2661 | 14.7674 | 38.8876 | 79.6262 | 79.6262 |

What is claimed is:

1. A process for the recovery of an olefin from a gas feed stream comprising hydrocarbons and minor amounts of olefins, which process comprises:
 a) introducing the gas feed stream into a single recovery distillation column having an upper tray section and with an overhead condenser and reflux drum;
 b) withdrawing an overhead vapor stream from said column;
 c) cooling and partially condensing the overhead vapor stream in the overhead condenser, to provide an overhead vapor-liquid;
 d) phase-separating the overhead vapor-liquid in the reflux drum;
 e) withdrawing from the reflux drum, an olefin-lean, overhead vapor stream and recycling the separated liquid from the reflux drum to the column;
 f) withdrawing from said column, a liquid $C_3+$, $C_4+$, $C_5+$, or $C_6+$ bottoms product stream;
 g) recycling at least a portion of the liquid bottoms product stream to the overhead condenser or the upper tray section of said column, to maintain the temperature of the overhead condenser above about $-140°$ F. refrigeration temperature; and
 h) withdrawing an olefin-rich, vapor phase, side product stream rich in a selected olefin.

2. The process of claim 1 wherein the gas feed stream comprises a refinery offgas stream derived from a Fuel Catalytic Cracker Unit (FCCU), or Coker unit, or mixture thereof.

3. The process of claim 1 which includes pretreating the gas feed stream by waterwashing, removing acid gases, and dehydrating the gas feed stream.

4. The process of claim 1 wherein the selected olefin comprises ethylene, propylene, or ethylene and propylene mixtures.

5. The process of claim 1 wherein the gas feed stream comprises up to about 20 percent (20%) by volume of ethylene and up to about 11 percent (11%) by volume of propylene.

6. The process of claim 1 for the recovery of propylene, ethylene, or ethylene-propylene mixtures, which process includes employing a carbon steel column, carbon steel shell and tube heat exchangers, and the process is free of employing turboexpanders.

7. The process of claim 1 which includes recovering, in the olefin-rich product side stream, greater than about 98 percent (98%) by volume of propylene in the gas feed stream and greater than about 90 percent (90%) by volume of ethylene in the gas feed stream.

8. The process of claim 1 which includes employing the overhead vapor stream for regeneration gas in dehydrating the gas feed stream or as a fuel gas.

9. The process of claim 1 which includes condensing the olefin-rich vapor side stream and recovering use ethylene, propylene, or ethylene-propylene mixtures.

10. The process of claim 1 wherein a selected olefin comprises ethylene, propylene, or ethylene-propylene mixtures, and heavy liquid bottoms stream comprises primarily $C_3+$ to $C_4+$ hydrocarbons.

11. The process of claim 1 wherein the selected olefin comprises propylene, ethylene, or ethylene-propylene mixtures, and the liquid recycle stream comprises primarily $C_5+$ to $C_6+$ hydrocarbons.

12. The process of claim 1 which includes maintaining the overhead condenser at a temperature range of about 0° F. to 140° F.

13. The process of claim 1 which includes recycling the column bottoms liquid stream in the molar ratio range from 0.03 to 1.0, with reference to the feed stream.

14. The process of claim 1 wherein the single column operates at a pressure of about 150 to 550 psig.

15. The process of claim 1 wherein the selected olefin comprises ethylene and which process includes maintaining the overhead condenser temperature at about −114° F. or warmer.

16. The process of claim 1 wherein the selected olefin comprises propylene and which process includes maintaining the overhead condenser temperature from about −40° F. or warmer.

17. The process of claim 1 wherein the feed gas steam comprises a synthesis gas stream produced by steam cracking of hydrocarbons for the production of ethylene.

18. The process of claim 1 which includes, intermediate the column in a side reboiler and below the point of feed stream introduction withdrawing, reboiling, and recycling a liquid side stream, to enhance the concentration of the selected olefin.

19. The process of claim 1 which includes withdrawing, in the side product vapor stream, ethane and propane with the selected olefin.

20. The process of claim 1 which includes removing the acid gas, in the gas feed stream, downstream of the recovery distillation column.

21. The process of claim 1 which includes employing the overhead vapor stream for the dehydration of the gas feed stream.

22. The process of claim 1 wherein the operating pressure of the recovery distillation column is about 250 to 260 psig.

23. A process for the recovery of an ethylene-propylene mixture or propylene from a refinery offgas feed stream, which process comprises:

a) introducing a waterwashed, dehydrated, refinery offgas feed stream, with acid gases removed, into a single recovery distillation column with an overhead condenser, reflux drum, and distillation trays, the offgas feed stream comprising $C_1+$ hydrocarbons, ethylene, and propylene;

b) withdrawing an overhead vapor stream from the recovery column;

c) cooling and partially condensing the overhead vapor stream in the overhead reflux condenser, to provide a vapor-liquid overhead stream;

d) phase-separating the vapor-liquid overhead stream in the reflux drum;

e) withdrawing from the reflux drum, a lean, stripped, overhead vapor stream essentially free of ethane, propane, ethylene and propylene;

f) withdrawing from, reboiling, and recycling to the column below the feed stream introduction, a side reboiler stream to enhance the concentration of the propylene and ethylene;

g) withdrawing a heavy liquid $C_3+$ to $C_6+$ product stream from the bottom of the recovery column and recycling at least a portion of the liquid product stream to the overhead condenser or upper tray section of the recovery distillation column, to maintain the temperature of the overhead condenser at a level of about 0° F. to −115° F.;

h) withdrawing a vapor side stream from the recovery column from trays between the side reboiler, the side stream comprising ethylene and propylene or propylene;

i) condensing the vapor side stream; and j) recovering the ethylene-propylene mixture or propylene as a condensed recovery product stream.

24. The process of claim 23 which includes withdrawing the liquid side stream from an intermediate upper tray of the column, recycling the reboiled side stream to the next lower tray of the column, and withdrawing the olefin-rich side product stream from between said intermediate upper and lower trays.

* * * * *